United States Patent [19]

Chou et al.

[11] Patent Number: 4,965,374

[45] Date of Patent: Oct. 23, 1990

[54] PROCESS FOR AND INTERMEDIATES OF 2',2'-DIFLUORONUCLEOSIDES

[75] Inventors: Ta-Sen Chou; Perry C. Heath; Lawrence E. Patterson, all of Indianapolis, Ind.

[73] Assignee: Eli Lilly and Company, Indianapolis, Ind.

[21] Appl. No.: 445,139

[22] Filed: Dec. 4, 1989

Related U.S. Application Data

[60] Division of Ser. No. 236,058, Aug. 24, 1988, abandoned, which is a continuation-in-part of Ser. No. 90,725, Aug. 28, 1987, abandoned.

[51] Int. Cl.$^5$ ............................................ C07D 307/32
[52] U.S. Cl. ................................. 549/313; 549/318; 536/23; 536/24; 536/26
[58] Field of Search .............................. 549/313, 318

[56] References Cited

U.S. PATENT DOCUMENTS

| | | | |
|---|---|---|---|
| 2,359,096 | 9/1944 | Elderfield | 549/313 |
| 2,607,800 | 8/1952 | Arundale | 560/111 |
| 4,526,988 | 7/1985 | Hertel et al. | 549/313 |
| 4,837,344 | 6/1989 | Miyaji et al. | 549/318 |
| 4,855,446 | 8/1989 | Duke et al. | 549/318 |

FOREIGN PATENT DOCUMENTS

| | | |
|---|---|---|
| 184365 | 6/1986 | European Pat. Off. . |
| 211354 | 2/1987 | European Pat. Off. . |
| 1055915 | 7/1951 | France .................... 549/313 |

OTHER PUBLICATIONS

Dowex::ION Exchange, The Dow Chemical Company, Midland, Mich., p. 71, 1959.

Encyclopedia of Polymer Science and Engineering, Second Edition, H. F. Mark et al., eds., John Wiley and Sons, New York, 1987, vol. 8, p. 346.

*Primary Examiner*—Glennon H. Hollrah
*Assistant Examiner*—Ba K. Trinh
*Attorney, Agent, or Firm*—Douglas J. Taylor; Leroy Whitaker

[57] ABSTRACT

The present invention provides a process for preparing lactone intermediates to 2',2'-difluoronucleosides whereby reversion back to the lactone's open chain precursor is minimized and the desired erythro enantiomer can be selectively isolated from an enantiomeric mixture of erythro and threo lactones in crystalline form. Also provided is a process for producing 2'-deoxy-2',2'-difluoronucleosides in about a 1:1 α/β anomeric ratio, and processes for selectively isolating β-2'-deoxy-2',2'-difluorocytidine, or an organic or inorganic acid addition salt thereof, from the 1:1 α/β mixture.

4 Claims, No Drawings

PROCESS FOR AND INTERMEDIATES OF 2',2'-DIFLUORONUCLEOSIDES

This application is a division of co-pending application 07/236,058, filed 08/24/88, now abandoned, which is a continuation-in-part of co-pending application 07/090,725, filed Aug. 28, 1987, now abandoned.

BACKGROUND OF THE INVENTION

U.S. Pat. No. 4,526,988 teaches that 2'-deoxy-2',2'-difluoronucleosides are useful antiviral agents. European Patent Application No. 184,365 teaches the use of the same compounds as oncolytic agents. The synthetic process disclosed in the publications produces intermediates containing up to two centers of chirality. One such intermediate having a chiral center is a protected lactone consisting of erythro and threo enantiomers of the formulae

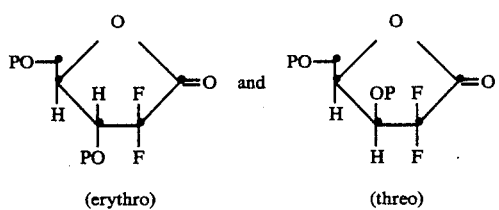

(erythro)                (threo)

wherein P is a protecting group. The publications teach the erythro enantiomer is preferred since it provides a carbohydrate which has the stereochemistry of naturally occurring ribose. A carbohydrate which has the stereochemistry of naturally occurring ribose is preferred since it provides final product nucleosides which exhibit superior biological activity.

U.S. Pat. No. 4,526,988 teaches the preparation of the above described erythio enantiomer by first forming an alkyl 2,2-difluoro-3-hydroxy-3-(2,2-dialkyldioxolan-4-yl)propionate, consisting of 3-R- and 3-S-hydroxy enantiomers, of the formulae

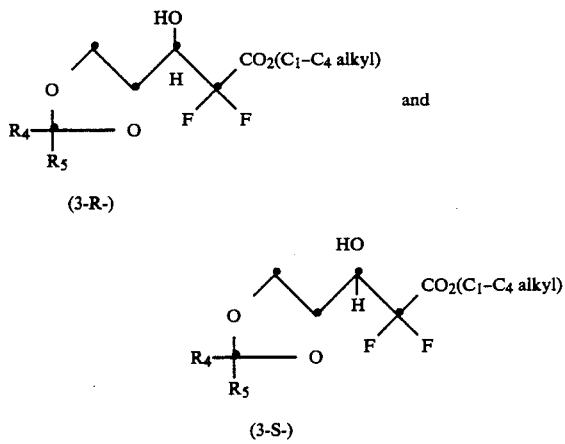

wherein $R^4$ and $R^5$ are independently $C_1$–$C_3$ alkyl, in a ratio of about 3 parts 3-R-enantiomer to about 1 part 3-S-enantiomer. The publication discloses that the 3-R-hydroxy enantiomer has the proper stereochemistry to provide the desired erythro enantiomer and that the 3-R- and 3-S-enantiomers can be separated by expensive, laborious column chromatography procedures.

The patent teaches that once the 3-R-hydroxy enantiomer is isolated it is next hydrolyzed under very mild conditions to form an unprotected lactone; namely, 2-deoxy-2,2-difluoro-D-erythro-pentofuranos-1-ulose, which has the formula

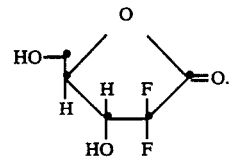

The publication teaches that mild conditions useful for forming the above compound include the use of hydrolysis reagents such as mildly acidic ion exchange resins or relatively strong acids, such as aqueous acetic acid or chloroacetic acid. Both types of hydrolysis reagents can cause problems in the hydrolysis reaction. For example, the use of ion exchange resin requires such large quantities of water that, especially in larger scale reactions, the lactone often reverts back to its open chain precursor because of its sensitivity to water. The relatively strong acids, on the other hand, are less preferred hydrolysis reagents for converting the 3-R- hydroxy enantiomer to the unprotected lactone since they produce large amounts of undesirable reaction products, including unreacted starting material.

Finally, once the unprotected lactone has been formed it is converted to the protected erythro lactone described above by adding an hydroxy protecting group to the lactone's hydroxy groups.

A second chiral center is produced at the anomeric carbon atom when the keto portion of the lactone is converted to an alcohol. More specifically, the two anomers for the desired erythro configuration are identified as α and β anomers of the formulae

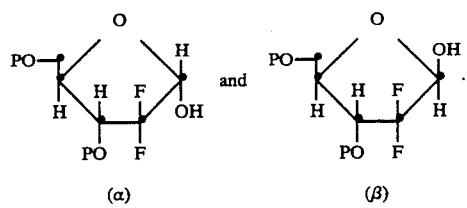

(α)                (β)

The unprotected hydroxy group at the 1-position is ultimately replaced by a heterocyclic base, such as cytosine, to provide protected precursors of the biologically active 2'-deoxy-2',2'-difluoronucleosides. The β anomer precursor is preferred since it provides 2'-deoxy-2',2'-difluoronucleosides which possess superior biological activity.

U.S. Pat. No. 4,526,988 specifically illustrates the use of t-butyldimethylsilyl as a protecting group. When this protecting group is used in the synthesis of 2'-deoxy-2',2'-difluoronucleosides the product is composed of about a 4:1 α/β anomeric ratio. This product must be purified by expensive, laborious column chromatography procedures to isolate the desired β anomer.

The present invention provides a convenient process for obtaining 2'-deoxy-2',2'-difluoronucleosides having the desired erythro and β stereochemistry which eliminates the need for extensive column chromatography purification, as previously required. Accordingly, one object of the present invention is to provide a process for preparing a crystalline lactone which is stable, therefore minimizing reversion back to the open chain precursor, as well as minimizing the formation of undesirable reaction products. Another object of the present invention is to provide a process for selectively isolating the erythro lactone from an enantiomeric mixture of erythro and threo lactones. Yet another object of this invention is to provide a process for producing the erythro configuration of 2'-deoxy-2',2'-difluoronucleosides in about a 1:1 α/β anomeric ratio. A final object of the invention is to provide processes for selectively isolating β-2'-deoxy-2',2'-difluorocytidine, or an organic or inorganic acid addition salt thereof, from about a 1:1 α/β anomeric mixture, such that approximately 99.0% pure β anomer is isolated.

SUMMARY OF THE INVENTION

This invention provides a process for preparing an enantiomeric mixture of erythro and threo lactones of the formula

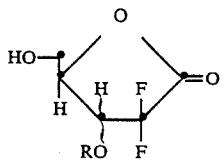

wherein R is H or

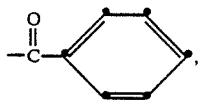

which comprises hydrolyzing a mixture of 3-R- and 3-S-enantiomers of an alkyl 2,2-difluoro-3-hydroxy-3-(2,2-dialkyldioxolan-4-yl)propionate, or a protected derivative thereof of the formula

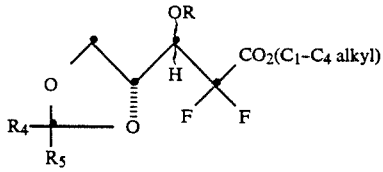

wherein R is as defined above and $R^4$ and $R^5$ are independently $C_1$–$C_3$ alkyl, by using a strong acid as a hydrolytic reagent, followed by azeotropic distillation of water.

This invention also provides a process for selectively isolating, in greater than about 95.0% purity, 2-deoxy-2,2-difluoro-D-erythro-pentofuranos-1-ulose-3,5-dibenzoate, which has the formula

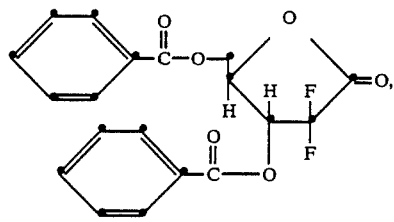

from an enantiomeric mixture of erythro and threo lactones of the formula

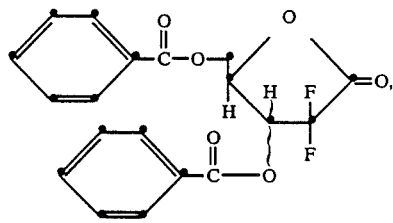

comprising dissolving the enantiomeric mixture in methylene chloride, cooling the solution to a temperature in the range of about −5° C. to about 10° C., and collecting the precipitated erythro enantiomer.

Yet another embodiment of the present invention is a process for producing a 2'-deoxy-2',2'-difluoronucleoside of the formula

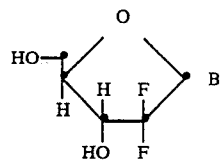

wherein B is a base of the formula

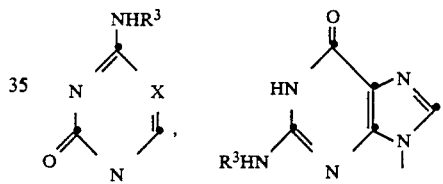

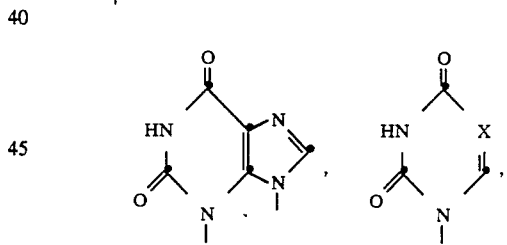

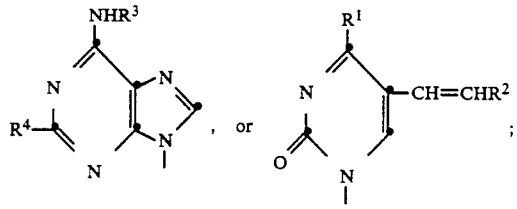

X is N or C—$R^4$;
$R^1$ is hydroxy or amino;
$R^2$ is bromo, chloro or iodo;
$R^3$ is hydrogen, $C_1$–$C_4$ alkyl or

$R^4$ is hydrogen, $C_1-C_4$ alkyl, amino, bromo, fluoro, chloro or iodo; and $R^5$ is hydrogen or $C_1-C_4$ alkyl; in about a 1:1 $\alpha/\beta$ anomeric ratio comprising reacting a protected carbohydrate of the formula

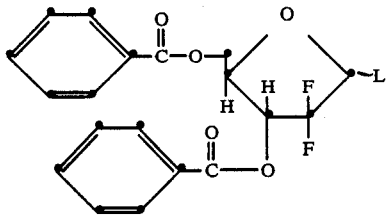

wherein L is a leaving group, with an appropriate base B-H, and removing the benzoyl protecting group by reaction with a strong or moderately strong base.

This invention also provides a process for selectively isolating $\beta$-2'-deoxy-2',2'-difluorocytidine hydrochloride or hydrobromide which is at least about 80.0% pure from about a 1:1 $\alpha/\beta$ anomeric mixture of 2'-deoxy-2',2'-difluorocytidine hydrochloride or hydrobromide comprising dissolving the 1:1 $\alpha/\beta$ mixture in hot water, adding acetone, cooling the solution to a temperature in the range of about $-10°$ C. to about 50° C., and collecting the precipitated $\beta$-2'-deoxy-2',2'-difluorocytidine hydrochloride or hydrobromide salt. $\beta$-2'-Deoxy-2',2'-difluorocytidine hydrochloride or hydrobromide thus prepared may be further purified by repeating the process set forth above, on the salt collected above, to provide approximately 99.0% pure $\beta$-2'-deoxy-2',2'-difluorocytidine hydrochloride or hydrobromide.

Finally, this invention provides a process for selectively isolating $\beta$-2'-deoxy-2',2'-difluorocytidine which is about 99.0% pure from about a 1:1 $\alpha/\beta$ anomeric mixture of 2'-deoxy-2',2'-difluorocytidine, or an organic or inorganic acid addition salt thereof, comprising dissolving the $\alpha/\beta$ mixture in hot water, increasing the pH of the aqueous solution to about 7.0 to about 9.0, cooling the solution to a temperature in the range of from about $-10°$ C. to about 30° C., and collecting the precipitated $\beta$-2'-deoxy-2',2'-difluorocytidine free base. $\beta$-2'-Deoxy-2',2'-difluorocytidine free base thus prepared may be converted to a pharmaceutically acceptable organic or inorganic acid addition salt by a process comprising dissolving the free base collected above in hot water, adding a pharmaceutically acceptable organic or inorganic acid to the solution, cooling the solution to a temperature in the range of from about $-10°$ C. to about 40° C., and collecting the precipitated, approximately 99.0% pure, $\beta$-2'-deoxy-2',2'-difluorocytidine acid addition salt.

DETAILED DESCRIPTION OF THE INVENTION

U.S. Pat. No. 4,526,988 discloses alkyl 2,2-difluoro-3-hydroxy-3-(2,2-dialkyldioxolan-4-yl)propionates of the formula

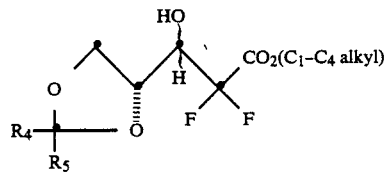

wherein $R^4$ and $R^5$ are independently $C_1-C_3$ alkyl. The compounds consist of 3-R- and 3-S-hydroxy enantiomers in a ratio of about 3 parts 3-R-enantiomer to 1 part 3-S-enantiomer. The present invention provides a process for converting the above compounds, or protected derivatives thereof, of the formula

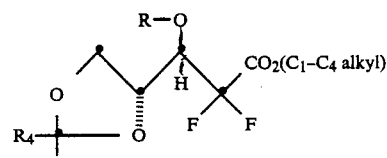

wherein R is H or

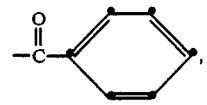

to a lactone of the formula

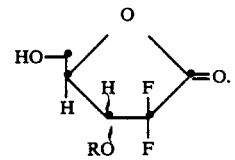

The protected derivative starting material noted above can be prepared by reacting the unprotected alkyl 2,2-difluoro-3-hydroxy-3-(2,2-dialkyldioxolan-4-yl)propionate with benzoyl bromide, chloride, cyanide, or azide. The reaction is conveniently carried out at temperatures in the range of from about $-10°$ C. to about 50° C. in an inert solvent to which an acid scavenger, such as a tertiary amine, has been added. The reaction may also be carried out in a basic solvent such as pyridine, quinoline, isoquinoline, or lutidine, or in a tertiary amine solvent such as triethylamine, tributylamine, methylpiperidine, or the like. Additionally, a catalyst such as 4-dimethylaminopyridine or 4-pyrrolidinopyridine may be used in the reaction, if desired.

The 3-hydroxy compounds, or their benzoyl protected derivatives, are converted to the lactone in the following manner. First, the isoalkylidene protecting group is selectively removed to form an alkyl 2,2-difluoro-3,4,5-trihydroxypentanoate or alkyl 2,2-difluoro-3-(benzoyloxy)-4,5-dihydroxypentanoate compound of the formula

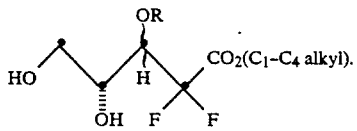

The selective removal of the isoalkylidene protecting group is achieved by using a strong acid as a hydrolytic reagent. The term "strong acids", as defined herein, are acids which have a pKa at room temperature (22° C.) of about −10.0 to about 2.0. Examples of strong acids include inorganic acids such as 1 to 8 normal hydrochloric acid, 1 to 8 normal sulfuric acid, and the like, and organic acids such as p-toluenesulfonic acid, trifluoroacetic acid, and the like. Preferred strong acids are those acids which have a pKa of about 31 7.0 to about 0.0. Particularly preferred strong acids are 6N sulfuric acid, trifluoroacetic acid and p-toluene-sulfonic acid. The strong acid is generally employed in catalytic quantities, although greater than catalytic quantities can be employed if desired. Typically the acid is employed in an amount sufficient to provide about 0.05 to about 0.5 molar equivalents of acid relative to the alkyl 2,2-difluoro-3-hydroxy-3-(2,2-dialkyldioxolan-4-yl)propionate, or protected derivative, starting material.

The propionate starting material and the strong acid are dissolved in a suitable solvent and the water content of the solution is adjusted to provide from about 1 to about 5 molar equivalents of water relative to the propionate starting material. Suitable solvents include polar solvents such as the alcohols, for example methanol, ethanol, isopropanol, and the like; acetonitrile; and related polar solvents. The water content of the solution can be adjusted to provide between about 1 to about 5 equivalents of water in several ways; by adding additional water to the water already present in the organic or inorganic strong acid, by choosing an inorganic acid which has the proper normality to provide the desired quantity of water, or by choosing a solvent, such as 95% ethanol, which contains a small amount of water. In general, about 1 to 2 molar equivalents of water relative to the propionate starting material are preferred since the lower water content is easily removed when cyclizing to the lactone.

After the propionate starting material, the strong acid, the solvent and water have been mixed, the solution is heated in order to begin selective removal of the isoalkylidene protecting group. The solution is preferably heated to the reflux temperature of the reaction mixture. The isoalkylidene protecting group is substantially removed after about 2 hours to about 8 hours when the reaction is conducted at the preferred temperature.

Once the isoalkylidene protecting group has been substantially removed the resulting pentanoate is cyclized to the desired lactone. The pentanoate is cyclized by distilling a water/alcohol, a water/acetonitrile, or a water/acetonitrile/aromatic solvent azeotropic mixture in order to remove water from the reaction solution. When an alcohol is used as the solvent the water/alcohol distillation preferably should continue until substantially all of the water and alcohol have been removed. However, when acetonitrile is used as the solvent fresh acetonitrile and/or aromatic solvent is added in order to ensure that sufficient solvent is present in order to drive out the water and any non-solvent volatile components, yet still maintain a homogeneous liquid solution. Preferably, an aromatic solvent, such as toluene, is used in place of fresh acetonitrile when removing water from an acetonitrile solvent solution since less solvent is then required to azeotropically dry the solution. Once the water has been substantially removed from the reaction mixture the pentanoate cyclizes to the lactone in high yield. This cyclization reaction can be monitored by high performance liquid chromatography assay techniques in order to determine when the reaction is substantially complete. The lactone produced consists of erythro and threo enantiomers in approximately the same enantiomeric proportions as present in the propionate starting material.

The present invention also provides a process for selectively isolating the erythro enantiomer of a protected derivative of the above lactone from an enantiomeric mixture of protected compounds.

Before isolating the erythro enantiomer the unprotected hydroxy groups of the above lactone (C-3 and C-5 if a 3-hydroxy propionate starting material was used to prepare the lactone, only C-5 if the benzoyl protected starting material was used) are protected with a benzoyl protecting group. The protected lactone is prepared by reacting the unprotected lactone with benzoyl chloride, bromide, cyanide, or azide using conditions disclosed in U.S. Pat. No. 4,526,988. Once the protected lactone is prepared the erythro enantiomer can be isolated by dissolving the enantiomeric mixture in methylene chloride. While the erythro enantiomer can be isolated from methylene chloride alone, the use of an isopropanol or hexane counter-solvent will increase the amount of erythro enantiomer which can be recovered. Accordingly, isopropanol/methylene chloride and hexane/methylene chloride solvent mixtures are preferred for isolating the erythro enantiomer.

When an isopropanol or hexane counter-solvent is used, the isopropanol or hexane may be added to the solution of enantiomeric mixture dissolved in methylene chloride all at once, or slowly over a period of time ranging from 5 minutes to 4 hours. The specific time for slowly adding the counter-solvent will, of course, be influenced by the amount of counter-solvent added. If isopropanol is used as counter-solvent, the amount of isopropanol added may vary from that needed to obtain an isopropanol/methylene chloride solvent mixture of from about 5 parts by volume of isopropanol to about 1 part by volume methylene chloride to about 20 parts by volume of isopropanol to about 1 part by volume of methylene chloride. If hexane is used as counter-solvent, it may be added in any amount up to that which will produce a hexane/methylene chloride solvent mixture of from about 5 parts by volume of hexane to about 1 part by volume of methylene chloride. A hexane/methylene chloride solvent mixture of about 3:2, v:v, hexane:methylene chloride is most preferred.

After the protected lactone has substantially dissolved in the methylene chloride, and any desired counter-solvent has been added, the solution is seeded with a crystal of authentic 2-deoxy-2,2-difluoro-D-erythro-pentofuranos-1-ulose-3,5-dibenzoate, and cooled to a temperature in the range of about −5° C. to about 10° C., more preferably to about 0° C. The cold solution is stirred, while maintaining the desired temperature, for about 30 minutes to about 5 hours and the desired erythro enantiomer is isolated, typically by filtration, using standard isolation techniques.

Occasionally, and with greater frequency when the counter-solvent is added all at once, the erythro enantiomer will begin to crystallize immediately upon counter-solvent addition. When this happens, the isolated product often is less than 95.0% purity 2-deoxy-2,2-difluoro-D-erythro-pentofuranos-1-ulose-3,5-dibenzoate. The purity of this less than 95.0% material can be improved by slurrying the impure material in an aromatic solvent such as toluene. The slurry is heated to about 40° C. to 50° C., dissolving substantially all of the desired erythro enantiomer and very little of the undesired impurities. The non-dissolved impurities are then removed using any standard isolation technique, such as filtration, to provide a solution. The aromatic solvent is removed to provide a residue, which is dissolved in methylene chloride. The erythro enantiomer is then recovered in greater than 95.0% purity following the procedures described above for isolating the erythro enantiomer from an erythro/threo enantiomeric mixture.

The isolated erythro enantiomer of the protected lactone is next converted to a compound of the formula

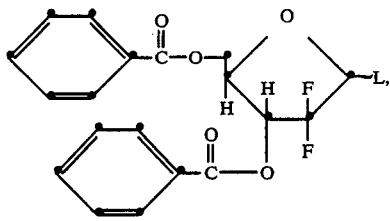

wherein L is a leaving group via procedures disclosed in U.S. Pat. No. 4,526,988. Appropriate leaving groups include the sulfonates such as methanesulfonate, toluenesulfonate, ethanesulfonate, isopropanesulfonate, 4-methoxybenzenesulfonate, 4-nitrobenzenesulfonate, 2-chlorobenzenesulfonate and the like; halogens such as chloro, bromo and the like; and other related leaving groups. A preferred leaving group for the process of this invention is methanesulfonate.

The above compound, having a leaving group as noted above, is reacted, per the process of the present invention, with a base of the formula

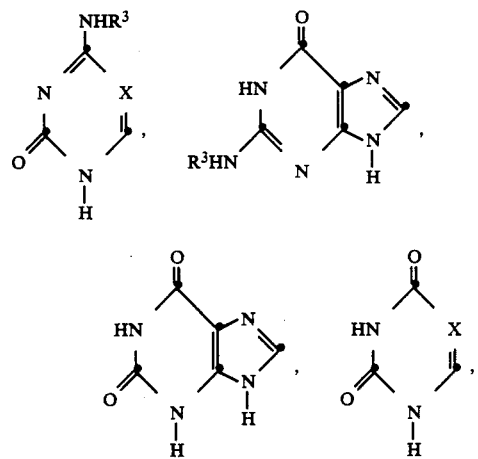

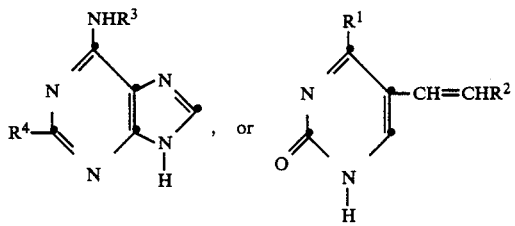

wherein
X is N or C—$R^4$;
$R^1$ is hydroxy or amino;
$R^2$ is bromo, chloro or iodo;
$R^3$ is hydrogen, $C_1$—$C_4$ alkyl or

$R^4$ is hydrogen, $C_1$-$C_4$ alkyl, amino, bromo, fluoro, chloro or iodo; and
$R^5$ is hydrogen or $C_1$-$C_4$ alkyl; to produce a 2'-deoxy-2',2'-difluoronucleoside in about a 1:1 α/β anomeric ratio.

The bases set forth above are commonly known to organic chemists, and no discussion of their synthesis is necessary. However, the primary amino groups, present on some of the bases, should be protected before the base is coupled with the carbohydrate. The usual amino-protecting groups, such as trimethylsilyl, isopropyldimethylsilyl, methyldiisopropylsilyl, triisopropylsilyl, t-butyldimethylsilyl, t-butoxycarbonyl, benzyloxycarbonyl, 4-methoxybenzyloxycarbonyl, 4-nitrobenzyloxycarbonyl, formyl, acetyl, and the like, may be used according to procedures described in standard textbooks, such as *Protective Groups in Organic Chemistry*, McOmie, Ed., Plenum Press, N.Y. (1973); and *Protective Groups in Organic Synthesis*, John Wiley & Sons, N.Y. (1981).

It is often advisable to convert keto oxygen atoms on the bases to the enol form in order to increase the base's aromaticity and thereby allow more ready attack of the base by the carbohydrate. Oxygen atoms are preferably enolized with the silyl protecting groups noted above.

The coupling reaction between base and carbohydrate may be carried out according to any of the procedures described in U.S. Pat. No. 4,526,988. A preferred coupling procedure uses a reaction initiator such as trimethylsilyltriflate, and a solvent such as 1,2-dichloroethane, at a temperature in the range of about 20° C. to about 100° C. The coupling reaction, substantially complete within about 2 hours to about 20 hours when conducted at a temperature in the range of about 20° C. to about 100° C., provides a protected nucleoside in about a 1:1 α/β anomeric ratio.

The same anomeric ratio of unprotected nucleoside is obtained by removal of protecting groups. Most silyl amino-protecting groups are easily cleaved using a protic solvent such as water or an alcohol. The benzoyl hydroxy-protecting group, and any acyl aminoprotecting groups, are removed by hydrolysis with a strong or moderately strong base at a temperature from about 0° C. to about 100° C. Strong or moderately strong bases suitable for use in this reaction are bases which have a pKa (at 25° C.) of about 8.5 to about 20.0. Such bases include alkali metal hydroxides such as sodium or potassium hydroxide; alkali metal alkoxides such as sodium methoxide or potassium t-butoxide; amines such as diethylamine, hydroxylamine, ammonia and the like; and other common bases such as hydrazine and the like. Preferably, the reaction employs ammonia to remove protecting groups at a temperature of about 10° C. At least one mole equivalent of base is needed for each protecting group removed. It is preferable to use an excess of base in this reaction. However, the amount of excess base used to remove the protecting groups is not crucial.

Removal of the hydroxy-protecting groups and amino-protecting groups is conveniently carried out in alcoholic solvents, especially aqueous alkanols such as methanol. However, the reaction may also be carried out in any convenient solvent, such as polyols including ethylene glycol, ethers such as tetrahydrofuran, ketones such as acetone and methyl ethyl ketone, or dimethylsulfoxide.

The preferred process for producing 2'-deoxy-2',2'-difluoronucleosides employs the base cytosine, which has the formula

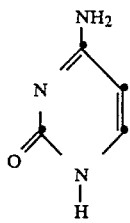

to provide 2'-deoxy-2',2'-difluorocytidine in about a 1:1 α/β anomeric mixture.

As noted above, the present invention finally provides processes for selectively isolating β-2'-deoxy-2',2'-difluorocytidine, or an organic or inorganic acid addition salt thereof, in approximately 99.0% purity from about a 1:1 α/β 2'-deoxy-2',2'-difluorocytidine anomeric mixture.

One process for selectively isolating the β anomer, utilizes a hydrochloride or hydrobromide salt of the 1:1 α/β anomeric mixture as starting material. The hydrochloride or hydrobromide salt of the α/β mixture is isolated by combining the 1:1 α/β mixture with isopropanol, and heating when necessary, to dissolve the anomeric mixture in the solvent. The amount of isopropanol used, while not critical, should be sufficient to effect complete dissolution of the anomeric mixture once hydrochloric or hydrobromic acid addition is complete, but yet be as minimal as possible to avoid excessive product loss during crystallization and isolation. The preferred amount of isopropanol used will be from about 2 ml of solvent per gram of anomeric mixture to about 12 ml of solvent per gram of anomeric mixture.

Once the anomeric mixture is substantially dissolved in the solvent, hydrochloric or hydrobromic acid is added to form either the hydrochloride or hydrobromide salt of the α and β anomers. Any undissolved anomeric mixture will dissolve after the acid is added to the isopropanol solution. Reagent grade concentrated liquid hydrochloric acid and fourty-eight percent aqueous hydrobromic acid are preferred forms of hydrochloric and hydrobromic acids for use in preparing the hydrochloride or hydrobromide α and β salts. The amount of acid added is not critical so long as at least a slight molar excess of acid is used relative to the anomeric mixture. Preferably two mole equivalents of hydrochloric or hydrobromic acid are used for each mole equivalent of the anomeric mixture.

After the acid is added the α and β hydrochloride or hydrobromide salts will begin to crystallize. If a smaller quantity of 1:1 α/β anomeric mixture, for instance less than 5.0 grams, is used in preparing the hydrochloride or hydrobromide salt, the β anomer will selectively crystallize relative to the α anomer. Thus, small quantities of a 1:1 α/β anomeric mixture can be purified to provide 2'-deoxy-2',2'-difluorocytidine hydrochloride or hydrobromide which has at least about a 1:4 α/β anomeric ratio simply by combining the 1:1 α/β anomeric mixture with isopropanol, adding hydrochloric or hydrobromic acid to the mixture, cooling the solution to a temperature in the range of about −10° C. to about 50° C., and collecting the precipitated solid.

However, when larger quantities of the 1:1 α/β anomeric mixture are used to prepare the hydrochloride or hydrobromide salt, the α and β salts precipitate in approximately the same 1:1 ratio as present in the α/β mixture. To obtain the α and β salts in high yield the solution should be cooled to a temperature in the range of from about −10° C. to about 50° C. The approximately 1:1 α/β 2'-deoxy-2',2'-difluorocytidene hydrochloride or hydrobromide thus precipitated is isolated, typically by filtration, from the solution using standard isolation techniques and may be purified to provide approximately 99.0% β anomer as set forth below.

The 1:1 α/β anomeric salt mixture is first dissolved in hot water. The temperature of the hot water is not critical, but it is preferred that the water temperature be from about 50° C. to about reflux (100° C.). A preferred hot water temperature is about 80° C. The concentration of anomeric salt mixture in the water is not critical as long as sufficient water is employed to ensure total dissolution. It is preferred that the amount of water employed be as minimal as possible to avoid excessive product loss during crystallization and isolation. Appropriate concentrations of the anomeric salt mixture in water vary from about 50 mg of mixture per ml of water to about 400 mg of mixture per ml of water. The preferred concentration used in the isolation of the β anomer is about 200 mg of anomeric salt mixture per ml of water.

Once the anomeric salt mixture is dissolved in the water, acetone is added to the hot solution to form a solvent mixture. The composition of the solvent mixture may vary from about 7 parts by volume of acetone to 1 part by volume of water to about 30 parts by volume of acetone to 1 part by volume of water. A composition of about 12:1, v:v, acetone:water is preferred. After acetone addition, the β anomer will begin to crystallize. In order to obtain the β anomer in high yield the solution should be cooled to a temperature in the range of about −10° C. to about 50° C., preferably from about 0° C. to about 15° C. The cooled solution is stirred, while maintaining the desired temperature, for about 30 minutes to about 24 hours and 2'-deoxy-2',2'-difluorocytidine hydrochloride or hydrobromide which has at least about a 1:4 α/β anomeric ratio is isolated, typically by filtration, from the solution using standard isolation techniques.

The 1:4 anomeric mixture thus isolated can be further purified, if desired, by repeating the procedure used to prepare the 1:4 α/β anomeric mixture, described above. Thus, β-2'-deoxy-2',2'-difluorocytidene hydrochloride or hydrobromide may be obtained in approximately 99.0% purity by dissolving β-2'-deoxy-2',2'-difluorocytidene hydrochloride or hydrobromide which is at least 80.0% pure in hot water, adding acetone, cooling the solution to a temperature in the range of about −10° C. to about 50° C., and collecting the precipitated solid.

A second process for selectively isolating an acid addition salt of β-2'-deoxy-2',2'-difluorocytidine from about a 1:1 α/β anomeric mixture of 2'-deoxy-2',2'-difluorocytidine utilizes the solubility difference between the free base forms of the α and β anomers, in a slightly basic aqueous solution, to selectively isolate β-2'-deoxy-2',2'-difluorocytidine. Once the free base form of the β anomer is isolated, it is easily converted to an organic or inorganic acid addition salt.

Isolation of the free base form of the β anomer is a preferred process for selectively isolating acid addition salts of β-2'-deoxy-2',2'-difluorocytidine since the β anomer can be recovered in higher yields than provided by previously known processes. Additionally, isolation of the free base form of the β anomer can be used to improve product purity since the free base form of the β anomer selectively crystallizes relative to both the free base form of the α anomer, as well as any additional impurities (such as ammonium triflate and inorganic salts such as magnesium sulfate and the like) present in the 1:1 α/β anomeric mixture.

The free base form of the β anomer is isolated by dissolving the 1:1 α/β anomeric mixture, or an organic or inorganic acid addition salt thereof, in hot (about 45° C. to about 90° C.) water. To aid dissolution of the non-salt form of the anomeric mixture, the pH of the water may be adjusted to about 2.5 to about 5.0 using common organic or inorganic acids such as hydrochloric acid or the like. If an acid addition salt of the anomeric mixture is used a common organic or inorganic base such as sodium hydroxide or the like may be used to adjust the pH of the water to about 2.5 to about 5.0 in order to aid dissolution. The amount of water used, while not critical, should be sufficient to effect complete dissolution of the anomeric mixture or its salt, but yet be as minimal as possible to avoid excessive product loss during crystallization and isolation.

Organic or inorganic acid addition salts of the 1:1 α/β anomeric mixture included within the scope of this process include salts formed from organic acids such as tartaric acid, citric acid, acetic acid and the like, as well as salts formed from inorganic acids such as hydrochloric acid, hydrobromic acid, sulfuric acid, phosphoric acid and the like. The hydrochloride and hydrobromide acid addition salts are especially preferred in the process of the present invention. Such salts of the 1:1 α/β anomeric mixture can be prepared by processes well known to those skilled in the art, for example, by the process for preparing a hydrochloride or hydrobromide salt of the 1:1 α/β anomeric mixture as discussed above.

Once the anomeric mixture, or its salt, is substantially dissolved in the water, the pH of the hot solution is increased to about 7.0 to about 9.0 using a common organic or inorganic base such as sodium hydroxide or the like. Preferably, the pH of the aqueous solution will be increased to about 8.0 to about 8.5. After the pH has been increased to the desired value, the solution is allowed to cool. To obtain the free base form of the β anomer in high yield the solution should be cooled to a temperature in the range of from about −10° C. to about 30° C. The solution, optionally seeded with authentic crystals of β-2'-deoxy-2',2'-difluorocytidine if desired, is then stirred for about 30 minutes to about 24 hours. The β-2'-deoxy-2',2'-difluorocytidine thus crystallized is isolated from the solution using standard isolation techniques, typically by filtration, in about 99.0% purity.

β-2'-Deoxy-2',2'-difluorocytidine thus prepared can be converted to a pharmaceutically acceptable organic or inorganic acid addition salt by dissolving the β anomer in hot (about 45° C. to about 90° C.) water. The amount of water used, while not critical, should be sufficient to effect complete dissolution of the α anomer, but yet be as minimal as possible to avoid excessive product loss during crystallization and isolation. The pH of the water may be adjusted to about 2.5 to about 5.0 using a pharmaceutically acceptable acid to aid in dissolving the β anomer, if desired.

Once the β anomer is substantially dissolved, a pharmaceutically acceptable organic or inorganic acid is added to form an acid addition salt. Pharmaceutically acceptable organic or inorganic acids contemplated within the scope of this invention include organic acids such as tartaric acid, citric acid, acetic acid, benzoic acid and the like, and inorganic acids such as hydrochloric acid, hydrobromic acid, sulfuric acid, phosphoric acid and the like. Hydrochloric acid and hydrobromic acid are preferred acids for use in the present process. The amount of acid added is not critical so long as at least a slight molar excess of acid is used relative to the free base form of the β anomer.

After the acid is added the acid addition salt of β-2'-deoxy-2',2'-difluorocytidine will begin to crystallize. To obtain the salt of the β anomer in high yield the solution should be cooled to a temperature in the range of from about −10° C. to about 40° C., preferably from about 0° C. to about 15° C. The solution, optionally seeded with authentic crystals of the 2'-deoxy-2',2'-difluorocytidine salt if desired, is then stirred for about 30 minutes to about 24 hours. Finally, the product is isolated, typically by filtration, from the solution using standard isolation techniques to provide a pharmaceutically acceptable acid addition salt of 2'-deoxy-2',2'-difluorocytidine in about 99.0% purity.

The following Examples illustrate specific aspects of the present invention. The Examples are not intended to limit the scope of the invention in any respect and should not be so construed.

EXAMPLE 1

Preparation of an enantiomeric mixture of D-erythro- and D-threo-2-deoxy-2,2-difluoropentofuranos-1-ulose-3-benzoate To a 2 liter flask fitted with a reflux condenser were added 104 g (0.27 mole) of 96.0% pure ethyl 2,2-difluoro-3-(benzoyloxy)-3-(2,2-dimethyldioxolan-4-yl)propionate which consisted of 3 parts of the 3-R-benzoyloxy enantiomer to 1 part of the 3-S-benzoyloxy enantiomer. Acetonitrile (1000 ml), deionized water (25 ml, 1.35 mole), and trifluoroacetic acid (6.4 g, 0.05 mole) were added. The resulting solution was heated to its reflux temperature (about 78° C.), and stirred at that temperature for 4 hours. After 4 hours the condenser was modified in order to allow the boiling liquid to distill rather than reflux. As the volatile acetonitrile, water, and trifluoroacetic acid distilled, fresh dry acetonitrile was added in order to maintain the solution volume at about 1000 ml. After a total of 3000 ml of liquid had distilled the solution was cooled to room temperature (22° C.).

The identity of the major components in the solution were characterized by a high performance liquid chromatographic (HPLC) comparison with authentic reference standards. The assay sample was prepared by placing 125 μl of the reaction solution in a 25 ml flask, adding 2 ml of isopropanol, and then diluting the resulting solution to 25 ml with hexane. The column was eluted with an elution solvent comprised of 6% by volume isopropanol and 94% by volume hexane. The column employed was a 25 cm Zorbax CN. The detector had a wavelength of 230 nm, the column flow rate was 2.0 ml/min, the injection volume was 10 μl. The HPLC assay established that the reaction solution contained a product assaying 87.2% by weight of an enantiomeric mixture of D-erythro- and D-threo-2-deoxy-2,2-difluoropentofuranos-1-ulose-3-benzoate. The HPLC assay also indicated the major impurities present were 2.7% by weight unreacted propionate and 5.5% by weight ethyl 2,2-difluoro-3-(benzoyloxy)-4,5-dihydroxypentanoate.

EXAMPLE 2

Preparation of an enantiomeric mixture of D-erythro- and D-threo-2-deoxy-2,2-difluoropentofuranos-1-ulose-3-benzoate To a 110 liter glass lined reactor were added 64 l of acetonitrile, 6.00 kg (16.2 mole) of a 3 part 3-R- to 1 part 3-S-enantiomeric mixture of ethyl 2,2-difluoro-3-(benzoyloxy)-3-(2,2-dimethyldioxolan-4-yl)propionate, 0.57 kg (4.4 mole) of trifluoroacetic acid, and 1500 ml (83.3 mole) of purified water. The resulting solution was heated to its reflux temperature (about 78° C.), and stirred at that temperature for 5½ hours. Next, 16 l of a solution of acetonitrile, water, and trifluoroacetic acid were distilled and replaced by 16 l of toluene. The resulting solution was heated to about 96.5° C. and an additional 16 l of volatiles were distilled. Fresh toluene (16 l) was added and the solution was heated to 96.5° C. again. The distillation, addition of fresh toluene, and heat to 96.5° C. process was repeated until 107 l of volatile constituents had distilled. The remaining solution was cooled to room temperature (22° C.) while maintaining a slight nitrogen bleed into the reactor to ensure that no moist air could enter the reactor during cooling. The resulting solution, characterized by the HPLC assay described in Example 1, contained a product assaying 81.8% by weight of an enantiomeric mixture of D-erythro- and D-threo-2-deoxy-2,2-difluoropentofuranos-1-ulose-3-benzoate. The HPLC assay indicated the major impurities present were 2.2% by weight unreacted propionate and 7.7% by weight ethyl 2,2-difluoro-3-(benzoyloxy)-4,5-dihydroxypentanoate.

EXAMPLE 3

A. Preparation of an enantiomeric mixture of D-erythro- and D-threo-2-deoxy-2,2-difluoropentofuranos-1-ulose-3,5-dibenzoate A solution of D-erythro- and D-threo-2-deoxy-2,2-difluoropentofuranos-1-ulose-3-benzoate dissolved in toluene was prepared according to the procedure of Example 2. This solution, assayed according to the HPLC assay described in Example 1, contained a product assaying 73.0% by weight D-erythro- and D-threo-2-deoxy-2,2-difluoropentofuranos-1-ulose-3-benzoate.

The solution was heated to 50° C. under reduced pressure to remove the toluene and provide 20.0 g (53.6 mmole) of the D-erythro- and D-threo-enantiomeric compound as an oil. The oil was transferred to a 500 ml flask and 100 ml of ethyl acetate and 11.6 g (146.8 mmole) of pyridine were added. Benzoyl chloride (10.3 g, 73.5 mmole) was dissolved in 100 ml of ethyl acetate and the resulting solution was added dropwise over 2 hours to the contents of the 500 ml flask. The reaction mixture was heated to about 60° C. and stirred at that temperature for 3½ hours, then cooled to room temperature (22° C.) and stirred overnight. The resulting mixture was washed successively with 200 ml of water, 200 ml of 1N hydrochloric acid, 200 ml of water, 200 ml of a saturated sodium bicarbonate solution, and 200 ml of a saturated sodium chloride solution, and then dried over anhydrous magnesium sulfate. The dried solution was concentrated under reduced pressure to provide 26.0 g of an oil. A representative sample of the oil was dissolved in acetonitrile and assayed using the HPLC procedure described in Example 1 to establish that the oil was composed of 52.0% by weight 2-deoxy-2,2-difluoro-D-erythro-pentofuranos-1-ulose-3,5-dibenzoate and 16.7% by weight of the corresponding D-threo enantiomer.

B. Isolation of 2-deoxy-2,2-difluoro-D-erythropentofuranos-1-ulose-3,5-dibenzoate The remaining oil prepared above was dissolved in 20 ml of methylene chloride. Hexane (30 ml) was added with stirring. The solution was seeded with authentic 2-deoxy-2,2-difluoro-D-erythro-pentofuranos-1-ulose-3,5-dibenzoate and an additional 25 ml of a 3:2 (v:v) hexane/methylene chloride solution were added. The resulting solution was cooled to about 0° C. for 15 minutes. The precipitated solid was collected by vacuum filtration and washed with 25 ml of a cold (0° C.) 3:2 (v:v) hexane/methylene chloride solution. The resulting crystals were dried in a vacuum oven at 40° C. for 3 hours to provide 9.0 g of the desired enantiomer, which was identified by N.M.R. analysis on a 300 mHz instrument in $CDCl_3$: δ=4.70 (singlet, 2H); 4.99 (singlet, 1H); 5.76 (singlet, 1H); 7.4–8.2 (broad multiplet, 10H). A representative sample of the dried crystals was dissolved in acetonitrile and assayed using the HPLC assay technique described in Example 1. The HPLC assay indicated that the product was 98.0% pure 2-deoxy-2,2-difluoro-D-erythro-pentofuranos-1-ulose-3,5-dibenzoate.

EXAMPLE 4

A. Preparation of an enantiomeric mixture of D-erythro- and D-threo-2-deoxy-2,2-difluoropentofuranos-1-ulose-3,5-dibenzoate A solution of 169.0 g (0.472 mole) of D-erythro- and D-threo-2-deoxy-2,2-difluoropentofuranos-1-ulose-3-benzoate (prepared according to the procedure of Example 2) dissolved in 845 ml of ethyl acetate was added to a 2-liter flask. Pyridine (111.5 g, 1.410 mole) was added to the flask and the solution was cooled to about 5° C. Benzoyl chloride (132.2 g, 0.940 mole) was dissolved in 300 ml of ethyl acetate and the resulting solution was added dropwise over 30 minutes to the 2-liter flask. The reaction mixture was allowed to warm to room temperature (22° C.) and stirred at that temperature overnight. The next morning the mixture was cooled to about 5° C. and the pyridine hydrochloride salts which had formed during the reaction were removed by filtration. The solution was then concentrated under reduced pressure to provide 249.0 g of an oil. A representative sample of the oil was dissolved in acetonitrile and assayed using the HPLC procedure described in Example 1 to establish that the oil was composed of 52.2% by weight 2-deoxy-2,2-difluoro-D-erythro-pentofuranos-1-ulose-3,5-dibenzoate and 14.9% by weight of the corresponding D-threo enantiomer.

B. Isolation of 2-deoxy-2,2-difluoro-D-erythro-pentofuranos-1-ulose-3,5-dibenzoate The remaining oil prepared above was dissolved in 174 ml of methylene chloride. Hexane (249 ml) was added over 30 minutes while the solution was stirred. The resulting solution was stirred at room temperature (22° C.) for 30 minutes and then cooled to about 5° C. and stirred at that temperature for an additional 30 minutes. The precipitated solid was collected by vacuum filtration and washed with 264 ml of a cold (0° C.) 3:2 (v:v) hexane/methylene chloride solution. The resulting crystals were dried in a vacuum oven at room temperature (22° C.) to provide 85.8 g of the desired enantiomer. The HPLC assay described in Example 1 established that the recovered crystals were 99.6% pure 2-deoxy-2,2-difluoro-D-erythro-pentofuranos-1-ulose-3,5-dibenzoate. m.p. 116°–118° C.

EXAMPLE 5

A. Preparation of an enantiomeric mixture of D-erythro- and D-threo-2-deoxy-2,2-difluoropentofuranos-1-ulose To a 500 ml flask were added 50.0 g (0.2 mole) of a 3 part 3-R- to 1 part 3-S-enantiomeric mixture of ethyl 2,2-difluoro-3-hydroxy-3-(2,2-dimethyldioxolan-4-yl)propionate, 250 ml of ethanol, and 6.0 ml of 6N sulfuric acid. The resulting solution was heated to its reflux temperature (about 76° C.), and stirred at that temperature for 3½ hours. After 3½ hours 100 ml of an ethanol/water mixture were distilled and replaced by 100 ml of fresh ethanol. The solution was cooled to room temperature (22° C.) and 4.5 g of anhydrous sodium carbonate were added. Ten minutes later 20 g of 3A molecular sieves were added. The resulting mixture was refrigerated overnight. The next morning the sodium carbonate and the molecular sieves were removed by filtration to provide a solution which, when characterized by the HPLC assay described in Example 1, was found to contain 231 mg of D-erythro- and D-threo-2-deoxy-2,2-difluoropentofuranos-1-ulose per ml of solution. Karl Fisher analysis of the solution indicated the water content was 0.9% by weight water.

B. Preparation of an enantiomeric mixture of D-erythro and D-threo-2-deoxy-2,2-difluoropentofuranos-1-ulose-3,5-dibenzoate The ethanol solution above was heated under reduced pressure to remove the ethanol. The resulting oil was dissolved in 100 ml of ethyl acetate. The solution was heated under reduced pressure to remove the ethyl acetate. The resulting gum was dissolved in 100 ml of methylene chloride. Karl Fisher analysis of the methylene chloride solution indicated the water content was about 0.09% by weight. The methylene chloride solution was diluted with an additional 225 ml of methylene chloride, followed by the addition of 2,6-lutidine (48.3 g, 0.45 mole) and 4-dimethylaminopyridine (3.0 g, 0.02 mole). The resulting solution was chilled in an ice bath to about 8° C. and benzoyl chloride (63.4 g, 0.45 mole) was added dropwise over the next 18 minutes at a rate which kept the reaction solution's temperature below about 15° C. After the benzoyl chloride was added the solution was allowed to warm to room temperature (22° C.) and 2,6-lutidine hydrochloride precipitated. The reaction mixture was washed successively with 250 ml of water, 250 ml of a 5% by weight sodium bicarbonate solution, 250 ml of 2N hydrochloric acid, and 250 ml of a saturated brine solution. The methylene chloride solution was then dried over anhydrous magnesium sulfate and assayed using the HPLC assay described in Example 1. The HPLC assay indicated that the methylene chloride solution contained 28.3 g of D-erythro- and D-threo-2-deoxy-2,2-difluoropentofuranos-1-ulose-3,5-dibenzoate.

C. Isolation of 2-deoxy-2,2-difluoro-D-erythro-pentofuranos-1-ulose-3,5-dibenzoate The methylene chloride solution prepared above was concentrated to a thick syrup by distillation. The syrup was redissolved in 30 ml of fresh methylene chloride. Isopropanol (300 ml) was added and the D-erythro product began to crystallize. Within ten minutes the product had precipitated to such an extent that a viscous slurry had formed. Additional methylene chloride (10 ml) and isopropanol (100 ml) were added in order to reduce the slurry's viscosity and the resulting mixture was refrigerated at 5° C. overnight. The precipitated solids were collected by vacuum filtration and washed successively with cold (0° C.) isopropanol and cold (0° C.) hexane. The resulting crystals were dried in a vacuum oven at 22° C. to provide 17.4 g of the D-erythro product, which was identified by N.M.R. analysis on a 300 mHz instrument in CDCl$_3$: $\delta$=4.70 (singlet, 2H); 4.99 (singlet, 1H); 5.76 (singlet, 1H); 7.4–8.2 (broad multiplet, 10H). The product, which melted at 119°–119.5° C., was believed to be greater than 95.0% purity 2-deoxy-2,2-difluoro-D-erythro-pentofuranos-1-ulose-3,5-dibenzoate.

EXAMPLE 6

A. Preparation of an enantiomeric mixture of D-erythro- and D-threo-2-deoxy-2,2-difluoropentofuranos-1-ulose-3,5-dibenzoate To a 250 ml flask were added 73 ml of a 2:1 (v:v) methanol/water solution which contained 2.33 g (13.89 mmole) of an enantiomeric mixture of D-erythro- and D-threo-2-deoxy-2,2-difluoropentofuranos-1-ulose (62.4% erythro enantiomer) prepared according to the procedure of Example 5. The solution was heated under reduced pressure to provide an oil. The oil was dissolved in 100 ml of ethyl acetate and the resulting solution was dried over anhydrous magnesium sulfate. After the magnesium sulfate was removed by filtration the solution was again concentrated under reduced pressure to provide a thick oil. This oil was dissolved in 18 ml of methylene chloride, followed by the addition of 0.17 g (1.38 mmol) of 4-dimethylaminopyridine. The solution was cooled to about 0° C. and 3.41 g (31.85 mmol) of 2,6-lutidine and 4.50 g (31.98 mmol) of benzoyl chloride were added. The solution was allowed to warm to room temperature (22° C.) and then stirred for about 64 hours. After stirring the solution volume was increased to about 50 ml with methylene chloride. The resulting solution was washed successively with 25 ml of a 5% by weight hydrochloric acid solution, 25 ml of a 5% by weight sodium bicarbonate solution, and 25 ml of water. The methylene chloride solution was dried over anhydrous magnesium sulfate and concentrated under reduced pressure to provide an oil. This oil, while not assayed, was believed to be the desired enantiomeric mixture of D-erythro- and D-threo-2-deoxy-2,2-difluoropentofuranos-1-ulose-3,5-dibenzoate.

B. Isolation of 2-deoxy-2,2-difluoro-D-erythro-pentofuranos-1-ulose-3,5-dibenzoate The above oil was dissolved in methylene chloride (3.5 ml). Isopropanol (35 ml) was added and the solution cooled to about 0° C. in an ice bath, then seeded with a crystal of the authentic compound. After stirring at about 0° C. for 3 hours the mixture was filtered. The filter cake was washed with cold isopropanol and room temperature (22° C.) hexane and dried in a vacuum oven at 22° C. to provide 0.87 g of 97.0% pure 2-deoxy-2,2-difluoro-D-erythro-pentofuranos-1-ulose-3,5-dibenzoate as established by the analytical technique described in Example 1. mp=117°-118° C. The product was also identified by N.M.R. analysis on a 300 mHz instrument in CDCl$_3$: $\delta$=4.70 (singlet, 2H); 4.99 (singlet, 1H); 5.76 (singlet, 1H); 7.4-8.2 (broad multiplet, 10H).

EXAMPLE 7

Preparation of a 1:1 $\alpha/\beta$ anomeric mixture of 2'-deoxy-2',2'-difluorocytidine To a 500 ml, 3-neck round bottom flask containing 250 ml of 1,2-dichloroethane were added 15.00 g (32.88 mmole) of 2-deoxy-2,2-difluoro-D-erythro-pentofuranos-3,5-dibenzoate-1-methanesulfonate, 15.65 g (52.60 mmole) of bis-trimethylsilyl-N-acetylcytosine, and 9.50 g (42.74 mmole) of trifluoromethanesulfonyloxytrimethylsilane. The solution was heated to reflux (84° C.) for about 8 hours. The reaction solution was cooled to room temperature (22° C.) and 100 ml of a 5% by weight hydrochloric acid solution added. After stirring for about 5 minutes the layers were separated and the water layer washed with 25 ml of methylene chloride. The organic layers were combined and washed successively with 100 ml of a 5% by weight sodium bicarbonate solution and 100 ml of a saturated brine solution. The resulting organic layer was dried over anhydrous magnesium sulfate and concentrated under reduced pressure to provide a foam.

Methanol (150 ml) was added to dissolve the foam. The solution was cooled to about 0° C. Ammonia gas was bubbled through the solution for about one minute. The volatile constituents were removed under reduced pressure to provide a gum. The gum was dissolved in 100 ml of ethyl acetate and 100 ml of water. The layers were separated and the organic layer was washed with 25 ml of water. Both aqueous layers were combined, washed with 100 ml of diethyl ether, and the aqueous solution was concentrated under reduced pressure to provide a gum. About 10 ml of methanol were added to dissolve the gum. The resulting solution was concentrated to dryness under reduced pressure to provide 4.14 g of 2'-deoxy-2',2'-difluorocytidine.

The product was characterized by an HPLC comparison with an authentic reference standard. The assay sample was prepared by placing 3 mg of product into a 5 ml volumetric flask and then diluting to volume with 0.1N hydrochloric acid. The column was eluted with an elution solvent comprised of 5% by volume methanol and 95% by volume 0.04M sodium acetate solution. The column employed was a 25 cm YMC type A-303. The detector had a wavelength of 275 nm, the column flow rate was 1.0 ml/min, the injection volume was 20 $\mu$l, and the column temperature was ambient (22° C.). The HPLC assay disclosed the product as approximately a 1:1 $\alpha/\beta$ anomeric mixture of 2'-deoxy-2',2'-difluorocytidine.

EXAMPLE 8

Preparation of 90.5% pure $\beta$-2'-deoxy-2',2'-difluorocytidine hydrochloride

An approximately 1:1 $\alpha/\beta$ anomeric mixture of 2'-deoxy-2',2'-difluorocytidine (1.86 g), prepared according to the procedure of Example 7, was dissolved in 6 ml of hot isopropanol (80° C.). Concentrated hydrochloric acid (15 drops) was added to the hot solution. The solution was seeded with authentic $\beta$-2'-deoxy-2',2'-difluorocytidine hydrochloride, allowed to cool to room temperature, and refrigerated over the weekend. The mixture was filtered and the filter cake was washed with isopropanol and vacuum dried at 22° C. to provide 0.38 g of a product which assayed as 90.5% pure $\beta$-2'-deoxy-2',2'-difluorocytidine hydrochloride by the analytical procedure described in Example 7. The product was also identified by N.M.R. analysis on a 300 MHz instrument in CDCl$_3$: $\delta$=3.81 (triplet, 2H); 3.93 (doublet, 1H); 4.23 (triplet, 1H); 4.80 (doublet, 2H); 6.08 (doublet, 1H); 6.32 (doublet, 1H); 8.21 (doublet, 1H); 9.0 (singlet, 1H); 10.17 (singlet, 1H).

Additional crystals formed in the filtrate upon sitting overnight at room temperature. These L crystals were recovered and dried as described above to provide an additional 0.17 g of 82.0% pure $\beta$-2'-deoxy-2',2'-difluorocytidine hydrochloride as established by the above HPLC procedure.

EXAMPLE 9

Preparation of 99.4% pure $\beta$-2'-deoxy-2',2'-difluorocytidine hydrochloride

To a 50 ml flask fitted with a reflux condenser were added 100.0 mg of 2'-deoxy-2',2'-difluorocytidine hydrochloride (88.7% pure $\beta$ anomer prepared according to the procedure of Example 8) and 0.5 ml water. The mixture was heated to reflux (100° C.) and all solids dissolved. While the solution was refluxing 10 ml of acetone were added. The solution was cooled to room temperature and refrigerated overnight. The mixture was filtered and the resulting crystals were dried in a vacuum oven at 22° C. to provide 69.0 mg of 99.4% pure $\beta$-2'-deoxy-2',2'-difluorocytidine hydrochloride as established by the analytical technique described in Example 7. The N.M.R. spectrum of this material was identical to that described in Example 8.

EXAMPLE 10

Preparation of 79% pure
β-2'-deoxy-2',2'-difluorocytidine hydrobromide

An approximately 1:1 α/β anomeric mixture of 2'-deoxy-2',2'-difluorocytidine (300 mg), prepared according to the procedure of Example 7, was substantially dissolved in 3 ml of hot isopropanol (60° C.). Aqueous hydrobromic acid (0.3 ml of a 48% by weight solution of hydrobromic acid dissolved in water) was added to the hot solution and all the remaining solids dissolved. An additional 1 ml of isopropanol was added and the solution was refrigerated overnight. The mixture was filtered and the filter cake was washed with isopropanol and vacuum dried at 22° C. to provide 110 mg of a product which assayed as 79.0% pure β-2'-deoxy-2',2'-difluorocytidine hydrobromide by the analytical procedure described in Example 7. (The only change from the analytical procedure of Example 7 was that 0.1N hydrobromic acid was used to dilute the present sample to volume rather than 0.1N hydrochloric acid.) The product had the following elemental analysis.

Analysis calc. for $C_9H_{12}N_3O_4F_2Br$: Theory: C, 31.41; H, 3.52; N, 12.21; F, 11.04; Br, 23.22; Found: C, 29.54; H, 3.64; N, 11.02; F, 10.90; Br, 23.16.

EXAMPLE 11

Preparation of a 1:1 α/β anomeric mixture of
2'-deoxy-2',2'-difluorocytidine hydrochloride A. Preparation of a 1:1 α/β anomeric mixture of
2'-deoxy-2',2'-difluorocytidine To a 500 ml, 3-neck round bottom flask containing 200 ml of 1,2-dichloroethane were added 10.0 g (65.7 mmole) of N-acetylcytosine, 12.0 g (74.5 mmole) of 1,1,1,3,3,3-hexamethyldisilazane (HMDS) and 0.47 g (4.38 mmole) of chlorotrimethylsilane (CTMS). The slurry was heated to reflux (84° C.) and within 15 minutes a solution was obtained. The solution was refluxed for about one hour and then the solvent was removed to provide a thick residue.

The thick residue was dissolved in 200 ml of 1,2-dichloroethane. To the solution were added 19.55 g (88.0 mmole) of trifluoromethanesulfonyloxytrimethylsilane, 3.6 g (22.2 mmole) of HMDS and 2.4 g (22.1 mmole) of CTMS. The solution was stirred at room temperature (22° C.) for 30 minutes and 58 ml of a solution of 2-deoxy-2,2-difluoro-D-erythro-pentofuranos-3,5-dibenzoate-1-methanesulfonate dissolved in 1,2-dichloroethane (0.345 grams of methanesulfonate per ml of solvent; total methanesulfonate 20.0 g) were added. The solution was heated to reflux (84° C.) for about 18 hours then cooled to room temperature (22° C.) and 10 ml of methanol and 145 ml of water were added. After stirring for about 5 minutes the layers were separated and the organic layer was again combined with 145 ml of water. The layers were separated once more, and the two water layers were combined and washed with 25 ml of 1,2-dichloroethane. The organic layer from above was combined with the dichloroethane wash and the combination washed successively with 145 ml of a 5% by weight sodium bicarbonate solution and 145 ml of water. The resulting organic layer was dried over anhydrous magnesium sulfate and concentrated under reduced pressure to provide a foam.

Methanol (220 ml) was added to dissolve the foam. The solution was cooled to about 5° C. and ammonia gas (6.0 g) was bubbled through the solution. The volatile constituents were removed under reduced pressure to provide an oily residue. The residue was dissolved in 145 ml of ethyl acetate and 145 ml of water. The layers were separated and the organic layer washed twice with 50 ml of water. The aqueous layers were combined, and the resulting solution was concentrated to dryness under reduced pressure to provide 8.4 g of an approximately 1:1 α/β anomeric mixture of 2'-deoxy-2',2'-difluorocytidine, as established by the HPLC technique described in Example 7.

B. Preparation of a 1:1 α/β anomeric mixture of
2'-deoxy-2',2'-difluorocytidine hydrochloride The gum prepared above was dissolved in hot (60° C.) isopropanol. Reagent grade concentrated hydrochloric acid (5.1 ml) was added to the hot solution. The resulting solution was cooled to room temperature (22° C.) and refrigerated overnight. The resulting precipitate was collected by vacuum filtration, washed successively with cold (5° C.) isopropanol and room temperature hexane, and dried in a vacuum oven at 40° C. to provide 5.15 g of a compound which assayed as approximately a 1:1 α/β anomeric mixture of 2'-deoxy-2',2'-difluorocytidine hydrochloride by the HPLC technique set forth in Example 7.

EXAMPLE 12

Preparation of 97.7% pure
β-2'-deoxy-2',2'-difluorocytidine from a 1:1 α/β
2'-deoxy-2',2'-difluorocytidine hydrochloride anomeric
mixture Five grams of the approximately 1:1 α/β 2'-deoxy-2',2'-difluorocytidine hydrochloride anomeric mixture obtained in Example 11 were placed in a 100 ml round bottom flask containing 50 ml of hot (50° C.) water. Sodium hydroxide (2N) was added until the pH of the water was about 3.0, at which time all solids were dissolved. The pH of the aqueous solution was increased to about 8.2 using 5N sodium hydroxide. The basic solution was allowed to cool to room temperature (22° C.) and then refrigerated overnight. The precipitated solid was collected by vacuum filtration, washed with 5 ml of cold, pH 8.5, water, and dried in a vacuum oven at 40° C. to provide 1.65 g of a product which assayed as 97.7% pure β-2'-deoxy-2',2'-difluorocytidine by the HPLC technique described in Example 7.

EXAMPLE 13

Preparation of 98.8% pure
β-2'-deoxy-2',2'-difluorocytidine from a 1:1 α/β
2'-deoxy-2',2'-difluorocytidine anomeric mixture To 17 ml of hot (50° C.) water were added 8.4 g of a 1:1 α/β anomeric mixture of 2'-deoxy-2',2'-difluorocytidine prepared according to the procedure set forth Example 11. The pH of the resulting aqueous solution was increased to about 8.2 with 2N sodium hydroxide. The basic solution was cooled to room temperature (22° C.) and then refrigerated overnight. The precipitated solid was collected by vacuum filtration, washed with 5 ml of cold, pH 8.5, water, and dried in a vacuum oven at 40° C. to provide 1.4 g of a product which assayed as 98.8% pure β-2'-deoxy-2',2'-difluorocytidine by the HPLC assay technique set forth in Example 7.

EXAMPLE 14

Preparation of 100% pure
β-2'-deoxy-2',2'-difluorocytidine hydrochloride from
99.7% pure β-2'-deoxy-2',2'-difluorocytidine To a 500 ml four neck round bottom flask containing 100 ml of hot (55° C.) water were slowly added 20.0 g of 99 7% pure β-2'-deoxy-2',2'-difluorocytidine prepared according to the procedure of Example 12. Concentrated reagent grade hydrochloric acid was simultaneously added to the flask at a rate such that the pH of the aqueous solution was maintained at about 3.0 during the difluorocytidine addition. After the difluorocytidine addition was complete, an additional 13 ml of concentrated hydrochloric acid were added. The solution was cooled to about 0° C. in an ice bath and stirred at that temperature for about 3 hours. The precipitated solid was collected by vacuum filtration, washed successively with 5 ml of pH 1.0 water and 10 ml of acetone, dried in a vacuum oven at 45° C. to provide 21.3 g of a product which assayed as 100% pure β-2'-deoxy-2',2'-difluorocytidine hydrochloride by the HPLC assay technique described in Example 7. The product was further characterized by N.M.R. analysis on a 300 mHz instrument and had the same spectrum as the product described in Example 8.

We claim:

1. A process for selectively isolating, in greater than about 95.0% purity, 2-deoxy-2,2-difluoro-D-erythro-pentofuranos-1-ulose-3,5-dibenzoate, which has the formula

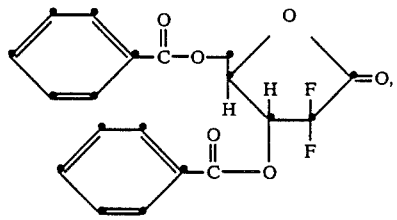

from an enantiomeric mixture of erythro and threo lactones of the formula

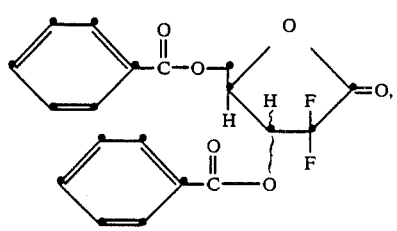

comprising dissolving the enantiomeric mixture in methylene chloride, cooling the solution to a temperature in the range of about −5° C. to about 10° C., and collecting the precipitated erythro enantiomer.

2. A process of claim 1 comprising the additional step of adding hexane to the solution of the enantiomeric mixture dissolved in methylene chloride to provide a hexane/methylene chloride solvent mixture.

3. The process of claim 2 wherein the solvent mixture comprises 3 parts by volume of hexane to 2 parts by volume of methylene chloride.

4. A process of claim 1 comprising the additional step of adding isopropanol to the solution of the enantiomeric mixture dissolved in methylene chloride to provide an isopropanol/methylene chloride solvent mixture.

* * * * *

UNITED STATES PATENT AND TRADEMARK OFFICE
CERTIFICATE OF CORRECTION

PATENT NO. : 4,965,374

DATED : October 23, 1990

INVENTOR(S) : T. S. Chou, et al.

It is certified that error appears in the above-identified patent and that said Letters Patent is hereby corrected as shown below:

Column 1, lines 43-60, the formulae which read

" 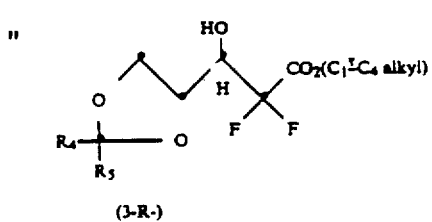 and 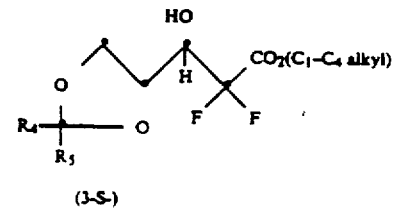 ", (3-R-)                                (3-S-)

should read

-- 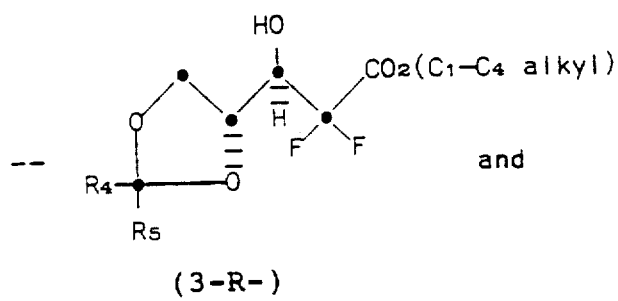 and 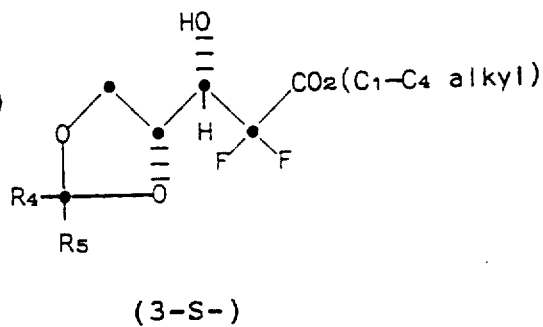 --

(3-R-)                                (3-S-)

UNITED STATES PATENT AND TRADEMARK OFFICE
CERTIFICATE OF CORRECTION

PATENT NO. : 4,965,374

DATED : October 23, 1990

INVENTOR(S) : T. S. Chou, et al.

It is certified that error appears in the above-identified patent and that said Letters Patent is hereby corrected as shown below:

Column 4, lines 21-29, the formula which reads

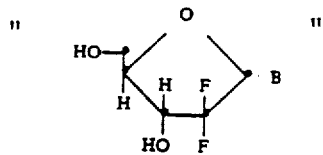

, should read

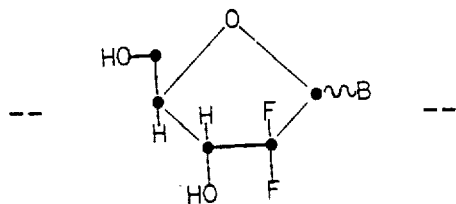

.

UNITED STATES PATENT AND TRADEMARK OFFICE
CERTIFICATE OF CORRECTION

PATENT NO. : 4,965,374                                    Page 3 of 3

DATED      : October 23, 1990

INVENTOR(S) : T. S. Chou, et al

It is certified that error appears in the above-identified patent and that said Letters Patent is hereby corrected as shown below:

Column 7, line 17, "31 7.0" should read -- -7. --.

Signed and Sealed this

Seventeenth Day of November, 1992

Attest:

DOUGLAS B. COMER

Attesting Officer      Acting Commissioner of Patents and Trademarks